US011026962B2

(12) United States Patent
Pietrzkowski

(10) Patent No.: US 11,026,962 B2
(45) Date of Patent: *Jun. 8, 2021

(54) BETALAIN COMPOSITIONS AND METHODS THEREFOR

(71) Applicant: VDF FUTURECEUTICALS, INC., Momence, IL (US)

(72) Inventor: Zbigniew Pietrzkowski, Aliso Viejo, CA (US)

(73) Assignee: VDF Futureceuticals, Inc., Momence, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/712,124

(22) Filed: Dec. 12, 2019

(65) Prior Publication Data

US 2020/0113922 A1 Apr. 16, 2020

Related U.S. Application Data

(63) Continuation of application No. 15/488,213, filed on Apr. 14, 2017, now Pat. No. 10,543,224, which is a continuation of application No. 14/726,379, filed on May 29, 2015, now Pat. No. 9,636,371, which is a continuation of application No. 13/056,482, filed as application No. PCT/US2009/052293 on Jul. 30, 2009, now Pat. No. 9,060,539.

(60) Provisional application No. 61/084,879, filed on Jul. 30, 2008, provisional application No. 61/140,541, filed on Dec. 23, 2008.

(51) Int. Cl.
| | |
|---|---|
| A61K 31/70 | (2006.01) |
| A01N 43/04 | (2006.01) |
| A61K 31/706 | (2006.01) |
| A61K 36/185 | (2006.01) |
| A23L 5/43 | (2016.01) |
| A23L 33/105 | (2016.01) |
| A61K 31/7056 | (2006.01) |
| A61K 36/21 | (2006.01) |
| A61K 9/00 | (2006.01) |

(52) U.S. Cl.
CPC ............ *A61K 31/706* (2013.01); *A23L 5/43* (2016.08); *A23L 33/105* (2016.08); *A61K 9/0053* (2013.01); *A61K 31/7056* (2013.01); *A61K 36/185* (2013.01); *A61K 36/21* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,027,042 | A | 5/1977 | von Elbe et al. |
| 4,127,676 | A | 11/1978 | Merensalmi |
| 4,238,518 | A | 12/1980 | Poisson |
| 4,409,254 | A | 10/1983 | Garin et al. |
| 5,514,666 | A | 5/1996 | Cerda et al. |
| 6,228,365 | B1 | 5/2001 | Kapadia |
| 2003/0036565 | A1 | 2/2003 | Parkin et al. |
| 2005/0181048 | A1 | 8/2005 | Romero |
| 2007/0196527 | A1 | 8/2007 | Jensen et al. |
| 2008/0268547 | A1 | 10/2008 | Avent et al. |
| 2011/0190230 | A1 | 8/2011 | Pietrzkowski |

FOREIGN PATENT DOCUMENTS

| | | |
|---|---|---|
| GB | 1559275 A | 1/1980 |
| GB | 2084603 A | 4/1982 |
| JP | 2004018828 A | 1/2004 |
| WO | 9826792 A1 | 6/1998 |
| WO | 2005053710 A2 | 6/2005 |
| WO | 2008094705 A1 | 8/2008 |

OTHER PUBLICATIONS

Bensen et al. Mayo Clinic Proceedings (1999), vol. 74, pp. 1095-1105.*
Allen, et al., "Compounding Capdules," Secundum Artem—Current and Practical Compounding Information for the Pharmacist, vol. 4, No. 4. Downloaded on Apr. 26, 2011.
AyurvedicCure.com, "Home Remedies for Sinusitis", http://www.ayurvediccure.com/home-remedies/homeremedies-sinusitis.htm, 2011; 3 pgs.
Berkow et al., The Merck Manual, 1992, pp. 1305-1307, 1338-1341, 1495-1497.
Database WPI, Week 200612, Thomson Scientific, London. GB; AN 2006-114292 XP002676347 & JP 2006 028029 A (Nippon Tensai Seito KK) Feb. 2, 2006 (abstract), 2 pages.
Diagnose-me.com, "Beetroot—Information and Recommended Uses," http://www.diagnose-me.com/treat/T303927.html, downloaded on Apr. 27, 2011; 3 pgs.
DietHealthClub.com, "Arthritis," Healthy Diet Plans, Health Issues and Diet, http://www.diethealthclub.com/health-issues-and-diet/arthritis.html, Waterfront Media, 2010.
Frank et al., "Urinary pharmacokinetics of betalains following consumption of red beet juice in healthy humans," Pharmacological Research, 2005; 52:290-297.
International Preliminary Report on Patentability for Application No. PCT/US2009/052293, dated Aug. 9, 2011; 8 pgs.
International Search Report and Written Opinion for Application No. PCT/US2009/052293, dated Oct. 26, 2009; 17 pgs.
Juicing-for-Health.com, "How to Get Rid of Acne Naturally," http://juicing-for-health.com/how-to-get-rid-of-acne.html, Downloaded on Oct. 14, 2013; 4 pgs.
Juurik, E., "Beetroot (*Beta vulgaris*) Rejuvenating & Medicinal Root," The Spring of Life, http://www.thespringoflife.net/beetroot.html. Downloaded on Apr. 27, 2011; 3 pgs.
Kanner, et al., "Betalains—A New Class of Dietary Cationized Antioxidants," J. Agric. Food Chem., 2001; 49:5178-5185.

(Continued)

*Primary Examiner* — Patrick T Lewis
(74) *Attorney, Agent, or Firm* — Martin Fessenmaier; Umberg Zipser LLP

(57) ABSTRACT

Contemplated compositions and methods employ betalains for treatment of various conditions, and especially osteoarthritis, sinusitis, contact dermatitis, acne, an allergic condition, reduced mental alertness, reduced physical strength, reduced physical endurance, and/or impaired mood.

20 Claims, No Drawings

(56) References Cited

OTHER PUBLICATIONS

Kuramoto, Yuichiro, et al. "Effect of Natural Food Colorings on Immunoglobulin Productionin Vitroby Rat Spleen Lymphocytes," Bioscience, Biotechnology, and Biochemistry, vol. 60, No. 10, 1996, pp. 1712-1713.

Lee, Y.N., et al. "Purification and Concentration of Betalaines by Ultra Filtration and Reverse Osmosis", Journal of Food Science, Wiley-Blackwell Publishing, Inc., Jan. 1, 1982; 47(2):465-471.

RawVeg.info, "Beets prevent cancer, heart disease, help liver detoxify," http://web.archive.org/web/20061231135107/http://rawveg.info/beets.html. Retrieved on Apr. 30, 2008; 2 pgs.

Strasser et al., "Pectic substances from red beet (*Beta vulgaris* L. var. *conditiva*). Part II. Structural characterization of rhamnogalacturonan II," Carbohydrate Polymers, 2002; 48:263-269.

Tesoriere, et al., "Absorption, excretion, and distribution of dietary antioxidant betalains in LDLs: potential health effects of betalains in humans," The American Journal of Clinical Nutrition, 2004; 80:941-945.

Trivieri, L et al., "Alternative medicine: the definitive guide", Random House Digital, Inc., p. 1012, 2002 (excerpt saved from http://books.google.com/books?id=x_eA7dClelgC&pg=PA1012&dq=alternative+medicine+-+beet+dermatitis&hl=en&ei=3IS3TZOXG5SusAPz-qyoAQ&sa=X&oi=book_result&ct=result&resnum=1&ved=0CEIQ6AEwAA#v=onepage&q=alternative%20medicine%20-%20beet%20dermatitis&f=false), Downloaded on Apr. 27, 2011.

VDF Futureceuticals, Inc., European Patent Publication EP08725107 published Nov. 11, 2009, Supplementary European Search Report dated Jun. 11, 2012, 1 pg.

Viable-Flerbal.com, "Beet Root", Viable Herbal Solutions, http://www.viable-herbal.com/singles/herbs/s804.htm, Downloaded on Apr. 27, 2011; 2 pgs.

Watson, J. R., "Seasonal changes in betalaine concentrations and genetic analyses of variation in betalaine and sugar concentrations in roots of table beets (*Beta vulgaris* L.)" Dissertation Abstracts International, University of Wisconsin, Madison, vol. 42. No. 5, Nov. 5, 1981, XP009159596, 1 page.

Wruss, Jurgen et al. "Compositional Characteristics of Commercial Beetroot Products and Beetroot Juice Prepared from Seven Beetroot Varieties Grown in Upper Austria." Journal of Food Composition and Analysis, vol. 42, 2015, pp. 46-55.

Yan-Xiang, G. et al., "Research progress on beltain," China Food Additives, Feb. 28, 2006; vol. 1:65-69.

Zielinska-Przyjemska, et al., "In vitro Effects of Beetroot Juice and Chips on Oxidative Metabolism and Apoptosis in Neutrophils from Obese Individuals," Phytotherapy Research, 2009; 23:49-55.

\* cited by examiner

BETALAIN COMPOSITIONS AND METHODS THEREFOR

This application is a continuation application of allowed U.S. patent application Ser. No. 15/488,213, filed Apr. 14, 2017, which is a continuation of U.S. Pat. No. 9,636,371, which is a continuation of U.S. Pat. No. 9,060,539, which is a national phase filing of PCT International Patent Application No. PCT/US09/52293, filed Jul. 30, 2009, which claims priority to U.S. provisional patent application with the Ser. No. 61/084,879, filed Jul. 30, 2008, and to U.S. provisional patent application with the Ser. No. 61/140,541, filed Dec. 23, 2008, both of which are incorporated by reference herein.

FIELD OF THE INVENTION

The field of the invention is compositions and methods for treatment of conditions in human, and especially to as they relate to betalain-containing compositions for treatment of osteoarthritis, acne, allergic conditions, sinusitis, and contact dermatitis. Compositions and methods contemplated herein also relate to use of the betalain-containing compositions as a non-caffeine stimulant.

BACKGROUND OF THE INVENTION

Osteoarthritis (OA) is a very common condition, and it is expected that about 80% of the U.S. population will have radiographic evidence of OA by age 65. Osteoarthritis is characterized by loss of articular cartilage that is frequently accompanied by pain and swelling of the tissue proximal to the affected joint, which in turn often leads to local or regional atrophy of muscles associated with that joint. Where OA has no identified underlying cause, OA is also referred to as primary or degenerative OA, while secondary OA is typically precipitated by various disorders or diseases (e.g., diabetes, local injury or infection, joint instability, etc.). In contrast, rheumatoid arthritis (RA) is a chronic, systemic autoimmune disorder in which the immune system attacks the affected joint, leading to significant inflammation and subsequent tissue degeneration.

Due to their different etiologies, RA and OA have distinct therapeutic approaches. For example, RA is typically treated with cyclosporine, methotrexate, or penicillamine, and is more severe cases with TNF-alpha or IL-1 blockers. To reduce inflammation, glucocorticoids and/or non-steroidal anti-inflammatory can be administered. On the other hand, OA is often treated with physical therapy, weight management, and/or various nutritional supplements. Among other supplements, methylsulfonylmethane, glucosamine and/or chondroitin sulfate have gained significant attention as supplements. More recently, various plant-derived supplements were described for treatment of OA. For example, WO 05/053710 teaches use of a drying process in the manufacture of glucosamine from various plant materials. In another example, a plant extract for treatment of osteoarthritis is prepared from *Morinda citrifolia* as described in U.S. Pat. App. 2007/0196527.

Most currently available energy drinks (e.g., Red Bull™, Rockstar™, Java Monster™, etc.) typically include significant quantities of caffeine and other methylxanthines, selected B vitamins (e.g., B3, B6, B12) and small molecule effectors (e.g., taurine, creatine, maltodextrin, glucuronolactone, etc.), as well as various herbal extracts/preparations (e.g., guarana, ginseng, ginkgo, yerba mate, etc.). Additionally, at least some of the currently marketed energy drinks also include substantial quantities of sugar.

Most of the stimulatory effect of such energy drinks is derived from caffeine, which is present in the average 8 ounce serving in an amount of about 80 mg. While an 80 mg dose of caffeine is generally not problematic for the average consumer, multiple servings of energy drinks tend to produce undesirable, and in some cases even dangerous side effects. For example, caffeine dosages above 250 mg tend to produce nervousness, irritability, sleeplessness, increased urination, arrhythmia, gastric irritation, and even loss of bone mass. Unfortunately, elimination of caffeine from the system typically results in a 'bummer' or crash, and sudden drops in caffeine levels from large doses have even been associated with seizures.

To overcome at least some of the problems associated with ingestion of large quantities of caffeine, other energy drinks are currently marketed (e.g., 5-Hour Energy®) that include large quantities of B-vitamins, amino acids (tyrosine, phenylalanine), taurine, glucuronolactone and only small quantities of caffeine. While such energy drinks typically avoid subjective discomfort upon caffeine elimination, other side effects are often encountered, including niacin flush and sleeplessness. Moreover, long-term effects of high-dose vitamin B administration is generally unknown.

Red beets have long been a common source of various nutrients, and particularly of sugar and betaine (i.e., trimethylglycine). Further useful compounds obtained from red beet include betalains, which represent a chemically diverse group of red to violet colored betacyanins (e.g., amaranthin, isoamaranthin, etc.) and typically yellow-colored betaxanthins (e.g., vulgaxanthin), which have found use as pharmaceutical and food coloring agents and as antioxidants. For example, betalains have been reported as antioxidants (see e.g., J Agric Food Chem. 2001 November; 49(11): 5178-85), which may have particular relevance to prevention of LDL cholesterol oxidation (see e.g., Free Radic Res. 2003 June; 37(6):689-96). More recently, as described in our copending International application WO 08/094705, betalain compositions were also found to be effective in reducing serum triglyceride concentration, inhibiting NF-kB, and stimulation of SIRT. Furthermore, red beet fiber has been reported to have numerous desirable properties when ingested, including reduction of total cholesterol and triglyceride levels, while increasing HDL cholesterol.

However, despite the numerous advantages of red beets and red beet extracts, red beets have not been reported as containing active compounds for treatment of OA, various allergic conditions or conditions associated with allergies, and lack of energy. Complicating matters with red beet extracts is their problematic manufacture and dispensation, especially where the red beet preparation is in dry form. Among other difficulties, betalains prepared from freeze-dried beet juice are often clumpy and highly hygroscopic. Therefore, such preparations are notoriously difficult to weigh out and aliquot, especially where relatively small quantities are distributed. Worse yet, most of the currently known dry betalain preparations are limited to betalain concentrations of about 1 wt % (total betalains), and almost all of the attempts to increase the betalain concentration by extraction or other means also leads to an increase of hygroscopicity and clumping. Alternatively, where red beet extracts are in liquid form, such extracts are often highly instable and tend to degrade rapidly.

Therefore, while numerous compositions and methods of red beet preparations are known in the art, all or almost all of them suffer from disadvantages. Consequently, there is still a need to provide improved compositions and methods for red beet preparations.

SUMMARY OF THE INVENTION

The present invention is directed to beet-derived compositions and methods in which such compositions are used for treatment of various conditions, and particularly osteoarthritis, acne, contact dermatitis, sinusitis, and/or conditions associated with allergy. Most preferably, contemplated compositions and methods will be enriched in betalains and have a reduced sugar content as compared to unprocessed beet juice.

In one preferred aspect of the inventive subject matter, a method of providing a product for human consumption will include a step of providing or including a quantity of betalains in a product for human consumption, wherein the quantity is effective to reduce at least one symptom associated with at least one of osteoarthritis, sinusitis, contact dermatitis, acne, an allergic condition, reduced mental alertness, reduced physical strength, reduced physical endurance, and impaired mood when the product is ingested at a recommended dosage and schedule. In a further step, a person is then instructed to orally administer the product at the recommended dosage and schedule to so reduce the at least one symptom associated with the condition. Most typically, the instruction will further inform the person that it is the quantity of betalains that is effective in the reduction of the symptom(s).

While not limiting to the inventive subject matter, it is generally preferred that the quantity of betalains is prepared from red beet, and/or that the quantity of betalains is included into the product as a solid preparation comprising total betalains at a concentration of at least 2 wt %, and more typically at least 10 wt %. It is also generally preferred that the solid preparation has a betalain to sugar ratio of at least 0.3, and more typically of at least 1.0. It is still further generally preferred that the dosage and schedule are selected such that the total daily intake of the composition provides between 10 mg and 50 mg total betalain. Thus, in especially contemplated aspects, the product is formulated as a nutritional supplement, wherein the supplement is formulated to provide between 10 and 250 mg of total betalains in a daily dose in which the supplement has a weight of less than 1000 mg.

Consequently, in another preferred aspect of the inventive subject matter, a method of treating osteoarthritis will include a step of administering to a person in need thereof betalains at a dosage and schedule effective to reduce at least one symptom associated with osteoarthritis. Most preferably, the dosage and schedule are selected such that the total daily intake of the betalains is between 10 mg and 50 mg, and where desired, the betalains are present in a composition isolated from a plant material wherein the composition has a betalain to sugar ratio of at least 1.0.

In a still further preferred aspect of the inventive subject matter, a method of providing a nutraceutical stimulant will have a step of providing betalains in the nutraceutical stimulant in a quantity effective to increase at least one of mental alertness, physical strength, physical endurance, and mood when the nutraceutical stimulant is ingested at a recommended dosage and schedule, and in another step, a person is instructed to orally administer the stimulant at the recommended dosage and schedule to so increase at least one of mental alertness, physical strength, physical endurance, and mood. It is generally preferred that the dosage and schedule are selected such that the total daily intake of the stimulant provides between 10 mg and 50 mg betalains, and/or that the betalains are added to the stimulant in a composition that is isolated from a plant material and that has a betalain to sugar ratio of at least 1.0.

Therefore, and viewed from a different perspective, use of a betalain-containing preparation is contemplated in the manufacture of an orally administered composition for treatment of osteoarthritis, sinusitis, contact dermatitis, acne, an allergic condition, reduced mental alertness, reduced physical strength, reduced physical endurance, and/or impaired mood. In especially preferred aspects, the betalain-containing preparation is a dried preparation having a betalain concentration of at least 5 wt %, and/or the betalain is included in the preparation in an amount of at least 15 mg per dosage unit.

Various objects, features, aspects and advantages of the present invention will become more apparent from the following detailed description of preferred embodiments of the invention.

DETAILED DESCRIPTION

The inventors have discovered that betalain-containing preparations, and especially various red beet preparations are suitable to reduce one or more symptoms associated with certain conditions, and especially osteoarthritis, sinusitis, contact dermatitis, acne, an allergic condition, asthma, reduced mental alertness, reduced physical strength, reduced physical endurance, and/or impaired mood.

Most preferably, the compositions and methods according to the inventive subject matter are orally administered such that a daily dosage of total betalains of between 10 mg and 250 mg is achieved. While preferred administration of the compositions contemplated herein is not restricted to a specific schedule or dosage, it is generally preferred that the compositions are administered over a period of at least 3 days, and more typically of at least 2 weeks, and most typically at least 1 month using oral administration preferably between once daily and three times daily.

In one exemplary preferred aspect it is contemplated that the beet preparation is prepared from red beet juice in an extraction process that produces a dry material at a concentration of betalains of at least 2 wt %, and more typically at least 5-10 wt % (e.g., see section examples and experiments below). Particularly preferred compositions are described and known from our International patent application WO 08/094705 (serial number PCT/US08/01418), which is incorporated by reference herein. Such preparation is then filled in capsules for oral administration of about 100 mg total preparation per capsule and orally administered three times daily over a period of at least three weeks.

For example, a betalain-containing composition was prepared following a protocol substantially as described in WO 2008/094705, which is incorporated by reference herein. Briefly, commercially available beet juice (about 65 brix; obtained from SVZ International) having a total betalain content of about 0.6 wt % on dry basis was filtered to remove particulates and the filtrate was used without further modification for chromatography. The filtrate was passed through a column packed with a hydrophobically modified styrene resin (commercially available as Resin HST-226 from VDF Futureceuticals) at between 1-50 bed volumes per hour at a loading with between 1-20 bed volumes. Pass fractions were discarded, and betalains were eluted from the resin using a mild buffer at slightly basic pH (e.g., 0.1-0.2 M ammonium acetate in water, pH 8.2 to 8.4, at a temperature of 110° F., or 0.1-0.2 M ammonium carbonate in water at pH range 7.0 to 9.0, same temperature). The so obtained eluate was freeze-dried without further modification to a dry product. Samples prepared according to the protocol above had a typical content as provided in Table 1 below:

TABLE 1

| Compound | Quantity |
| --- | --- |
| Total betalains | 27 wt % |
| Betaine | 30 wt % |
| Amino acids | 4 wt % |
| Fiber | 2 wt % |
| Protein | 6 wt % |
| Water | 8 wt % |
| Undetermined | 23 wt % |

It should be noted that the so prepared composition had a relatively high nitrogen content as measured by Kjeldahl and Folin-Ciocalteu. Notably, total nitrogen was present in the form of betaine (trimethylglycine), amino acids (which are most likely a mixture of free amino acids and amino acids covalently bound to one or more betalains), free ammonium ions and ammonium ion pairs as well as ammoniated compounds (and especially aminated betalains). Due to the relatively mild and rapid isolation process, it is also contemplated that the so isolated betalains have a relatively large fraction of carboxylated betalains (e.g., at least 50 mol %, more typically at least 80 mol %, most typically at least 90 mol % of total betalains, with 17-decarboxy-forms less than 10 mol %, more typically less than 5 mol %, and most typically less than 3 mol % of total betalains), all or at least some of which may contribute to the observed activities.

In still further contemplated aspects, it should be appreciated that numerous alternative preparations of betalain-containing compositions are deemed suitable and include those in which the total betalain concentration is at least 2 wt %, more preferably at least 5 wt %, even more preferably at least 10 wt %, and most preferably at least 20 wt %, typically at a betalain to sugar ratio of at least 0.3, more preferably at least 1.0, and most preferably at least 2.0. Moreover, it is generally preferred that the betalain-containing compositions will readily and substantially completely dissolve in water at fairly high concentrations (typically at least 90%-98% at 50-100 mg/ml). Still further it should be appreciated that while it is generally preferred that the betalain-containing compositions will be dried preparations, gels, and liquid preparations are also deemed suitable for use herein. Such preparations may be further processed to achieve a particular pH, consistency, or concentration of non-betalain components. In yet further aspects of the inventive subject matter, the betalains in the betalain-containing composition have a near natural composition (i.e., no individual betalain will be under- or over-represented by at least 10% as compared to composition prior to isolation).

Therefore, numerous other manners of producing betalain compositions are also deemed suitable and may use various materials as starting materials, including comminuted beet root or root peelings, root cell suspension culture, cactus pears, and even selected higher fungi. For example, where relatively low yields are acceptable, WO 98/26792 describes various methods of preparing betalain extracts from root pulp, while lyophilized beet is used as starting material as described in US 2003/0036565, which is subsequently ground, solvent extracted, and subjected to crosslinked dextran chromatography to yield distinct betalain fractions. Alternatively, beet juice concentrate may be spray dried to a powder comprising about 0.4 wt % betalains.

In other known methods (e.g., as described in U.S. Pat. No. 4,238,518 or GB patent 1 559 275), stabilized betanidine extracts are prepared using ion exchange chromatography while Garin et al. describe in U.S. Pat. No. 4,409,254 a process in which beet root extract is subjected at very low pH to chromatography using a non-ionic resin to so produce a concentrated eluate. Further suitable processes and products are described in U.S. Pat. No. 4,027,042 in which beet juice or beet pulp is subjected to a yeast fermentation and subsequent work-up.

Alternatively, it should be noted that numerous raw or starting materials other than red beet juice are also deemed suitable, and especially contemplated materials include raw red beet root or portions thereof (e.g., in solid, macerated, or paste form), red beet processing waste liquids, and red beet root cell cultures and culture supernatants. In still further contemplated aspects, suitable starting materials may also include plant materials that comprise betalains as a natural (or recombinantly produced) pigment. Therefore, betalain containing plants will also include those found in the order of the caryophyllales and selected basidiomycota, and in various cacti (e.g., prickly pear cactus and related plants). Consequently, it should be appreciated that depending on the type of starting material the exact composition of betalains may vary considerably. Additionally, it should be appreciated that the compositions according to the inventive subject matter may also comprise one or more individual isolated or synthetic betalains as sole or supplemental ingredient. However, it is generally preferred that the betalains in the preparation are a complex mixture of betalains with natural or near natural (i.e., deviation of each betalain of less than 10% as compared to natural composition) relative proportions.

In typical examples according to the inventive subject matter, the betalain-containing preparation has a total betalain concentration of at least 4.0 wt %, more typically at least 10.0 wt %, even more typically at least 15.0 wt %, and most typically at least 20.0 wt %. It should be noted that the chemical composition of the betalain preparations according to the inventive subject matter is a complex composition that includes a plurality of chemically distinct betalains. Thus, the complex preparation will include both betaxanthins and betacyanins. Most preferably, the betalain preparations presented herein have a near natural composition (i.e., no single betacyanin or betaxanthin originally present in the red beet is concentrated or depleted more than 30% [and more typically more than 15-20%] relative to the natural composition). Analysis of betalains and complex compositions can be performed as described by Corke et al (J Chromatogr Sci. 2005 October; 43(9):454-60) or Pourrat et al. (Journal of Food Science 53 (1), 294-295). Thus, typical preparations will include at least ten, more typically at least twenty, and most typically at least 25 chemically distinct betalains. Therefore, it should be noted that for various uses most commercially available betalain-containing preparations (e.g., juices, juice concentrates, powders) are also deemed suitable, although significantly higher overall quantities of those preparations may be needed (which in many cases will increase the dietary intake of sugars).

Depending on the particular source material and solvents used, it should be noted that the betalain to sugar ratio in contemplated compositions is least 0.3, more typically at least 0.5, even more typically at least 1.0, and most typically at least 2.0. Viewed from a different perspective, most preferred preparations will have a betalain to sugar ratio between 1.0 and 5.0, and even more typically between 2.5 and 4.5. With respect to the remaining sugars in contemplated compositions it should be recognized that the chemical nature will vary and depend on the starting material and work-up. However, most typical remaining sugars include may be mono-, oligo-, and/or polysaccharides, sugar alcohols, and pectins. Thus, it should be appreciated that where the oligo, and/or polysaccharide concentration is to be reduced, enzymatic or fermentative processes may be used to achieve such reduction. Alternatively, or additionally, residual monosaccharides may be removed using various manners known in the art, including ultrafiltration, molecular sieving, and/or enzymatic conversion.

With respect to the quantity of the beet preparation administered in a daily dose it is generally preferred that the amount of the preparation is between 1 mg and several hundred grams (or even more). However, and while not limiting the inventive subject matter, it should be noted that the preparations will typically be administered in an amount that is needed to provide an effective daily dose of betalains to reduce at least one symptom of the condition. Typically, the effective dose will be in the range of about 1 mg to about 1000 mg, more typically in the range of about 10 mg to about 500 mg, and most typically in the range about 25 mg to about 250 mg.

It is further contemplated that the preparations according to the inventive subject matter will be solid betalain-containing preparations that may be formulated in numerous manners. For example, suitable formulations include oral formulations (e.g., tablets, capsules, dragees, ready-to-mix formulation, etc.) in which the preparation is the primary ingredient or formulations in which the preparation is disposed in an edible carrier (e.g., bar, snack, confectionary item, etc.). Alternatively, the betalain-containing preparation may also be a liquid formulation in which the liquid is mixed or encapsulated in a nutritionally acceptable carrier. For example, suitable liquid formulations may include drinks, syrups, gelatin-encapsulated liquid extracts, oil infusions, soft gels, coatings for capsules, and liquid tinctures. Moreover, and especially where only a single betalain is used as the active ingredient, it is contemplated that the betalain may be formulated in a pharmaceutically acceptable formulation for oral or parenteral administration. In such case, especially suitable formulations include oral formulations, topical formulations, and formulations for injection.

Additionally, it should be appreciated that contemplated formulations/compositions for administration may also include a second compound that is known or reported to reduce symptoms of OA or symptoms of other conditions. For example, especially suitable second compounds include glucosamine, methylsulfonylmethane, and chondroitin sulfate where the preparation is provided as a nutritional supplement. On the other hand, where the preparation is provided as a pharmaceutical composition, the second compound may be a non-steroidal anti-inflammatory drug, a COX-inhibitor, etc. Consequently, contemplated compositions especially include those in which a single betalain or a plurality of chemically distinct betalains are formulated as an orally administrable composition, optionally in combination with another compound that is known or reported to reduce symptoms of OA. Such compositions may be formulated, for example, as a tablet or capsule, optionally in further combination with one or more vitamins, minerals, or herbal preparation, or as an edible product that is fortified with the betalain(s). For example, such products may be a snack, a bar, a candy, a drink, etc.

Therefore, administration of contemplated compositions is preferably oral using a daily dosage that contains about 1-250 mg, and most preferably between 10 and 100 mg of one or more betalains. The improvements in energy and alertness are observed in most cases after 3 days of continuous administration, whereas improvements in osteoarthritis and other conditions is typically observed after about 1 week. In most cases, administration will typically be between once daily and four times daily (or even more) with an amount of typically between 10 and 250 mg per dose. Therefore, especially preferred dosages will be between about 0.01 mg/kg to about 10 mg/kg (most preferably 0.1 mg/kg to about 1 mg/kg) body weight. While long-term administration is generally preferred, it should be appreciated that administration may extend over at least 3 days, more typically at least 1 week, even more typically at least 1 month, and most typically between 1 month and 6 months. Interestingly, discontinued use of contemplated compositions was not associated with any withdrawal symptoms normally found with energy drinks.

Experiments and Examples

Exemplary Processes for Extraction

Option 1: Extraction started with commercially available beet juice (about 65 brix; obtained from SVZ International) having a total betalain content of about 0.6 wt % on dry basis. The juice was filtered to remove particulates and the filtrate was used without further modification for chromatography. A column was packed with a hydrophobically modified silica resin (commercially available as Resin HSI-564 from VDF Futureceuticals; Momence, Ill. 60954), and the filtered juice was passed through the column at between 1-50 bed volumes per hour at a loading with between 1-20 bed volumes. The pass fractions were discarded, and the betalains were eluted from the resin using a mild buffer at slightly basic pH (e.g., 0.1-0.2 M ammonium acetate in water, pH 8.2 to 8.4, at a temperature of 110° F., or 0.1-0.2 M ammonium carbonate in water at pH range 7.0 to 9.0, same temperature). The so obtained eluate was freeze-dried without further modification to a dry product. Quantitative analysis of the product revealed a total betalain content of about 15 wt % at 6 wt % total sugar and a residual water content of about 8 wt %. The dry product was then ground using a rotating blade grinder to form a powder product that was passed through a 60 mesh sieve. More than 90%, and more typically more than 95% of the free-flowing dry product dissolved within less than 2 minutes at a concentration of between 0.1 mg/ml and 15 mg/ml, more typically at a concentration of between 10 mg/ml and 50 mg/ml, and more typically at a concentration of between 50 mg/ml and 100 mg/ml (and in some cases even higher, such as between 100 mg/ml and 200 ml/ml). Even more remarkably, the product was stable over at least 2 weeks storage at 75° F. and 50% relative humidity without any observable changes in composition, free-flowability, or other parameters, and did not aggregate to larger particles or clumps. Indeed, after 2 weeks (and longer) storage at the defined condition, substantially the same amount (>90%) of the dry powder passed through a mesh sieve of same mesh size.

Option 2: Extraction started as above with commercially available beet juice (about 65 brix; obtained from SVZ International) having a total betalain content of about 0.6 wt % on dry basis. The juice was filtered to remove particulates and the filtrate was used without further modification for chromatography. A column was packed with a hydrophobically modified styrene resin (commercially available as Resin HST-226 from VDF Futureceuticals) and the filtered juice was passed through the column at between 1-50 bed volumes per hour at a loading with between 1-20 bed volumes. The pass fractions were discarded, and the betalains were eluted from the resin using a mild buffer at slightly basic pH (e.g., 0.1-0.2 M ammonium acetate in water, pH 8.2 to 8.4, at a temperature of 110° F., or 0.1-0.2 M ammonium carbonate in water at pH range 7.0 to 9.0, same temperature). Without drying as described above, the so obtained eluate was mixed with a water-soluble polysaccharide (e.g., to about 30 wt % maltodextrin final concentration) as carrier and spray-dried to a dry product having about 10 wt % betalains at 45 wt % total sugar content with a residual water content of about 5 wt %. The average particle size of the spray-dried product was about 150 micron (passed through 60 mesh sieve). More than 90%, and more typically more than 95% of the free-flowing dry product dissolved within less than 2 minutes at a concentration of between 0.1 mg/ml and 15 mg/ml, more typically at a concentration of between 10 mg/ml and 50 mg/ml, and more typically at a concentration of between 50 mg/ml and 100 mg/ml (and in some cases even higher, such as between 100 mg/ml and 200 ml/m1). As above, the product was stable over at least 2 weeks storage at 75° F. and 50% relative humidity without any observable changes in composition, free-flowability, or other parameters, and did not aggregate to larger particles or clumps. Once more, after 2 weeks (and longer) storage at the defined condition, substantially the same amount (>90%) of the dry powder passed through a mesh sieve of same mesh size.

Analytic Tests

Betalain-rich red beet extract, (RBE) was prepared following the methods described in Options 1 and 2 above.

Proximate Analysis. Moisture content of RBE was determined according to USP loss-on-drying (LOD) method. Sample was heated in a vacuum oven at 70° C. for 7 hours. Total protein content was determined based on Bradford method. Available carbohydrates were calculated by deducting the sum of crude protein, crude fat, ash and moisture from 100% of the DM. Ash content was determined by igniting the sample at 550° C. in electric furnace, AOAC 923.03 (AOAC, 2005).

Mineral Analysis. The 1.2 g sample test portion was dry ashed at 500° C.±50° C. for 8 hours and treated with $HNO_3$. The resultant ash was treated with concentrated hydrochloric acid (5%), dried, and redissolved in hydrochloric acid solution (16). The amount of each element (Al, Ba, B, Ca, Cu, Fe, K, Mg, Mn, Na, Zn) was determined by comparing the emission of the unknown sample against the emission of each element from standard solutions using Inductively Coupled Plasma Atomic Emission Spectroscopy (ICAP-61E-Trace, Thermo Jarrell-Ash). All standard solutions used were obtained from Inorganic Ventures (Christiansburg, Va.—USA) and were of analytical-reagent grade.

Sugar Analysis. The sugars (sucrose, glucose, fructose, maltose, lactose, and galactose) were extracted from an accurately weighed sample with 80% ethanol by allowing it to stand for 24 hours with occasional swirling. Aliquots were dried under inert gas and reconstituted with a hydroxylamine hydrochloride solution in pyridine containing phenyl-β-D-glucoside as the internal standard. The resulting oximes were converted to silyl derivatives with hexamethyldisilazane (HMDS) and trifluoracetic acid (TFA) treatment and subsequently analyzed by gas chromatography using a flame ionization detector.

Total Dietary Fiber Analysis. Determination of total dietary fiber (TDF) was based on the methods of. Duplicate samples were cooked at ~100° C. with heat stable α-amylase to give gelatinization, and then digested with enzymes in a phosphate buffer to break down starch and some protein. Ethanol was added to each sample to precipitate any soluble fiber. The samples were filtered, and residues were rinsed with ethanol and acetone to remove starch and protein degradation products and moisture. Protein content was determined for one of the duplicates; ash content was determined for the other. The total dietary fiber in the sample was calculated after adjustment for the protein and ash values.

Amino Acid Analysis. A sample of RBE was hydrolyzed in hydrochloric acid (HCl) and adjusted to pH 2.2 for all amino acids except tryptophan. Tryptophan samples were hydrolyzed in sodium hydroxide and adjusted to pH 5.2. Individual amino acids were determined by comparison using an automated amino acid analyzer.

Fatty Acid Profile Analysis. Fat and fatty acids were extracted from RBE sample by hydrolytic method based on (23). Pyrogallic acid was added to minimize oxidative degradation of fatty acids during analysis. A triglyceride, triundecanoin (C11:0), was added as internal standard. Fat was extracted into ether, then methylated to fatty acid methyl esters (FAMEs) using BF3 in methanol. FAMEs were quantitatively measured by capillary gas chromatography (GC) against a C11:0 internal standard. Total fat was calculated as sum of individual fatty acids expressed as triglyceride equivalents. Saturated and monounsaturated fats were calculated as sum of respective fatty acids.

Vitamin Analysis. Vitamin C in the RBE sample was extracted, oxidized, and reacted with o-phenylenediamine to produce a fluorophor. The vitamin C content was determined by comparison of the sample extract fluorescence to the fluorescence of known standard. Beta carotene analysis was performed by HPLC method.

Total Betalain Quantification. Quantification of betalains was performed by a spectrophotometric multiple-component method of Nilsson using a UV-VIS spectrophotometer Shimadzu 1650 PC (Shimadzu Corporation, Kyoto, Japan). The determination of pigment concentration (i.e., betacyanins and betaxanthins) was calculated in terms of betanin and vulgaxanthin-I, respectively. The total pigment content (betalain) was expressed as the sum of betacyanin and betaxanthin components. Pigment content calculations were based upon the absorptivity values $A^{1\%}$ 1120 for betanin and 750 for vulgaxanthin-I.

Betalain Profile Analysis. 20 mg of RBE was shaken with 1 ml of water for 10 min under neutral gas in a 2 ml glass vial. Samples were centrifuged and supernatant was analysed directly by LC-DAD or LC-MS without any purification. A Gynkotek HPLC system with UVD340U, Gynkotek HPLC pump Series P580 and thermostat (Gynkotek Separations, H. I. Ambacht, The Netherlands) was used for chromatographic analysis. The analytical column was a Luna C-18(2) 250×3 mm I.D., 5 μm (Phenomenex, Torrance, Calif., USA). The following gradient system was used for the separation of analytes: 3% A in B at 0 min; gradient to 16% A in B at 17 min; gradient to 50% A in B at 30 min (A, acetonitrile; B, 2% formic acid in water). The injection volume was 10 μL and the flow rate of 0.5 mL/min was applied. Detection was generally performed at λ=538 nm with a UV-Vis detector or a DAD (diode array detection) system at 533, 505, and 480 nm, respectively (27). The columns were thermostated at 35° C. Positive ion electrospray mass spectra were recorded on a ThermoFinnigan LCQ Advantage mass spectrometer (San Jose, Calif., USA) at electrospray voltage 4.5 kV, capillary 250° C. and sheath gas: $N_2$ coupled to a ThermoFinnigan LC Surveyor pump applying in HPLC gradient System 1. The MS was controlled, and total ion chromatograms and mass spectra were recorded using ThermoFinnigan Xcalibur software (San Jose, Calif., USA).

Clinical Study Description and Design

This study was designed to be an open type clinical discovery rather than a clinical efficacy study. The primary goal was to verify whether RBE may improve pain and fatigue associated with osteoarthritis conditions. The secondary goal of this study was to identify Minimum Effective Dose (MED). Therefore, the inventor employed a multiple fixed-dose type study with three time points: (Day 1, 5, 10). There were 8 subjects per experimental group. Each group was treated with 100 mg (Group 1), 70 mg (Group 2) or 35 mg (Group 3) twice per day. All participants were asked to take one capsule of RBE 30 min prior to eating a meal.

Subjects for this study were selected randomly from a group of people who had been previously diagnosed with Osteoarthritis and who had reported symptoms characteristic of OA such as joint pain, limited joint flexibility, and feeling energy-depleted due to chronic pain and joint problems. The inventor used McGill pain score system and Energy Score system questionnaires at day 1, 5 and 10 as a means of quantifying symptoms.

Recruitment of subjects, treatments, blood sampling at day 1, 5 and 10, Mc-Gill and Energy score tests and blood chemistry were performed by Nutra Clinical, Inc. (San Diego, Calif., USA). Measurements of human cytokines and chemokines in collected sera were provided by Quensys, Inc. on research service basis. AOPP testing was performed on sera collected from subjects at day 1 and 10 days after the treatment in FutureCeutical's lab using commercially available kit (Cell Biolabs, Inc, USA).

Treatment of volunteers with contemplated compounds as used for OA for contact dermatitis, eczema, acne, and sinusitis was performed by twice daily administration of 100 mg of the above composition with subjective evaluation s indicated below.

Results

Nutritional composition of RBE. Red beet (*Beta vulgaris* L.) is commonly consumed as food product and FutureCeuticals' RBE is a specially processed extract obtained from this material. In Table 2 below, RBE is briefly compared with four different red beet products manufactured by other known concentration techniques. Due to the inventor's production process, the RBE material is depleted of sugars and enriched in total betalains up to 24%. More detailed basic chemical information about RBE is presented in Table 3.

TABLE 2

| | Concentration [%] | | | | | |
|---|---|---|---|---|---|---|
| Sample | Glucose | Fructose | Maltose | Sucrose | Total sugars | Total betalains |
| RBE | <0.1 | <0.1 | <0.1 | 0.2 | 0.5 | 24.6 |
| Freeze Dried Beet | 1.15 | 0.91 | 1.08 | 48.5 | 51.7 | 3.06 |
| Spray Dried Beet | 1.93 | 0.84 | ND[a] | 29.8 | 32.6 | 0.43 |
| Air Dried Beet | 0.71 | 0.74 | ND | 42.7 | 44.1 | 0.59 |
| Beet Juice Concentrate | 1.62 | 1.42 | ND | 41.3 | 44.4 | 1.65 |

TABLE 3

| Concentration [mg/100 g] | |
|---|---|
| Proximal constituents | |
| Moisture | 8.8 |
| Protein | 6.5 |
| Total Fat | 0.014 |
| Monosaturated Fatty Acids | 0.012 |
| Trans Fatty Acids | <0.007 |
| Polyunsaturated Fatty Acids | <0.007 |
| Saturated Fatty Acids | <0.007 |
| Ash | 2.04 |
| Total Carbohydrates | 13.8 |
| Dietary Fiber | 3.57 |
| Protein by Bradford method | 6.51 |
| Calories [cal/100 g] | 375 |
| Vitamins | |
| Vitamin A [IU/100 g] | <35.0 |
| Beta Carotene [mg/100 g] | <0.02 |
| Vitamin C [mg/100 g] | <1.0 |
| Amino acids | |
| Aspartic Acid | 132 |
| Cystine | 195 |
| Tryptophan | 644 |
| Methionine | 67.9 |
| Threonine | 49.2 |
| Serine | 57.2 |
| Glutamic Acid | 741 |
| Proline | <10.0 |
| Glycine | 297 |
| Alanine | 59.1 |
| Valine | 57.1 |
| Isoleucine | 26.3 |
| Leucine | 39.8 |
| Tyrosine | <10.0 |
| Phenylalanine | 44.7 |
| Lysine | 61.8 |
| Histidine | 45.6 |
| Arginine | 386 |
| Mineral elements | |
| Al | 3.71 |
| Ba | 0.73 |
| B | 1.21 |
| Cu | 3.28 |
| Fe | 28.9 |
| Mg | 152.0 |
| Mn | 13.4 |
| K | 50.6 |
| Ca | 74.8 |
| Na | 43.5 |
| Zn | 13.3 |

Betalain composition. The RBE sample was chromatographically analyzed to obtain a basic betalain profile (Table 4; [a] Peak area per injected sample measured at $\lambda_{max}$. Orientative data for relative comparison between the pigment signals). Because the profiles of the compounds can change during a purification process, and due to the possibility that some pigment degradation might occur, it was decided to analyze the samples directly after extraction with water. Only highly abundant basic compounds were listed in Table 4.

TABLE 4

| Peak No. | Compound | Retention time [min] | Peak area per injected sample measured at $\lambda_{max}{}^a$ (×10$^{-5}$) | $\lambda_{max}$ | m/z [M + H]$^+$ |
|---|---|---|---|---|---|
| 1 | Betanin | 16.9 | 12.6 | 535 | 551 |
| 2 | 17-decarboxy-betanin | 17.5 | 0.60 | 505 | 507 |
| 1' | Isobetanin | 18.2 | 15.6 | 535 | 551 |
| 2' | 17-decarboxy-isobetanin | 19.2 | 0.44 | 506 | 507 |
| 3 | Neobetanin | 22.3 | 3.9 | 464 | 549 |

Besides the highest peaks of betanin/isobetanin 1/1', a prominent peak of neobetanin 3, which had been frequently detected in *Beta vulgaris* L. roots, was also observed in the chromatogram. The presence of excessive amounts of 3 in betacyanin-bearing samples had been attributed many times to the degradation of betanin during processing of the samples; however, in this study, the pre-concentration factor was similar to that of betanin/isobetanin (data not shown) suggesting that the presence of 3 was rather a result of its enrichment than dehydrogenation of betanin. This effect is under investigation. Interestingly, the concentration of both diastereomers of betanin/isobetanin 1/1' was similar, indicating a possible epimerization during the whole process of extract concentration. The principal pigments 1/1' were mostly responsible for the total betalain content (24.6%) measured spectrophotometrically.

Further inspection of the chromatograms and mass ion traces revealed already known 17-decarboxylated betanins 2/2' present at lower levels in the concentrated extract. In comparison to the starting material, their enrichment factor was much higher than in the case of betanin (data not shown), which obviously could be a result of betanin degradation process. The presence of 2/2' has been frequently attributed to decarboxylation during heating of betanin solutions (27, 31-33); however, the degradation at room temperature cannot be excluded.

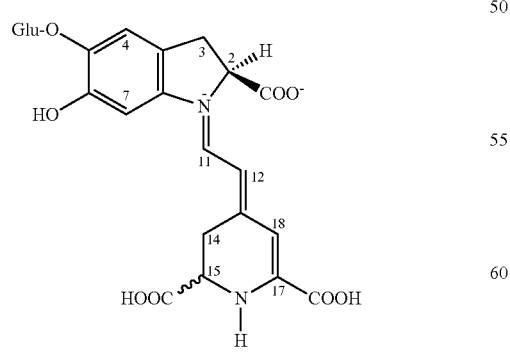

Betanin/Isobetanin (1/1')

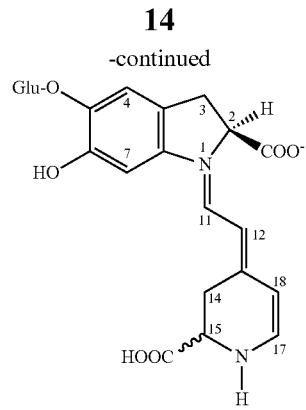

17-decarboxy-betanin/-isobetanin (2/2')

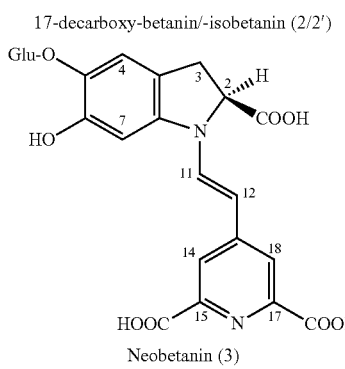

Neobetanin (3)

Effect of RBE on Pain Feelings as Measured Using McGill Test.

This study was performed to verify our hypothesis that betalain-rich food-grade material RBE may reduce discomforts associated with painful and swollen joints in people suffering Osteoarthritis. Collected results show that all subjects reported reduced pain level in the dose-dependent manner as measured by using McGill Questionnaire. Detailed data are provided in Table 5. Following these data, it is clearly noticeable that treatment with RBE resulted in a significant improvement of the Sensory part of McGill.

TABLE 5

McGill Scores

| Group | Sensory Part | | | Affective Part | | | Evaluative Part | | |
|---|---|---|---|---|---|---|---|---|---|
| Dose | Day 1 | Day 5 | Day 10 | Day 1 | Day 5 | Day 10 | Day 1 | Day 5 | Day 10 |
| Group 1 - 100 mg | | | | | | | | | |
| Average | 58.87 | 41.00* | 40.00* | 4.12 | 3.62 | 2.25* | 16.37 | 15.62 | 15.87 |
| StD | 3.31 | 4.40 | 7.21 | 1.80 | 2.19 | 1.48 | 3.42 | 4.83 | 4.45 |
| Max | 63 | 47 | 51 | 6 | 6 | 4 | 20.00 | 21.00 | 21.00 |
| Min | 53 | 35 | 30 | 1 | 1 | 1 | 10.00 | 8.00 | 8.00 |
| StE | 1.17 | 1.55 | 2.54 | 0.63 | 0.77 | 0.52 | 1.20 | 1.71 | 1.57 |
| Sum$^a$ | 471 | 328 | 320 | 33 | 29 | 18 | 131 | 125 | 127 |
| McGill Score | | | Day 1: 79.36; Day 5: 60.24; Day 10: 58.12 | | | | | | |
| Group 2 - 70 mg | | | | | | | | | |
| Average | 59.62 | 44.37* | 35.5* | 2.25 | 2.00 | 1.75 | 15.50 | 13.37 | 14.75 |
| StD | 5.57 | 10.68 | 4.72 | 2.31 | 1.69 | 0.70 | 3.89 | 3.96 | 2.81 |
| Max | 68 | 63 | 46 | 6 | 6 | 3 | 23 | 19 | 18 |
| Min | 53 | 35 | 32 | 1 | 1 | 1 | 12 | 9 | 10 |
| StE | 1.97 | 3.77 | 1.66 | 0.81 | 0.59 | 0.25 | 1.37 | 1.40 | 0.99 |
| Sum | 477 | 355 | 284 | 18 | 16 | 14 | 124 | 107 | 118 |
| McGill Score | | | Day 1: 77.37; Day 5: 59.74 Day 10: 52.00 | | | | | | |
| Group 3 - 35 mg | | | | | | | | | |
| Average | 63.25 | 56.12 | 54.62 | 2.25 | 2.12 | 2.37 | 21.87 | 20.25 | 21.75 |
| StD | 7.02 | 9.86 | 9.59 | 0.70 | 0.83 | 0.51 | 2.85 | 3.28 | 3.80 |
| Max | 75 | 70 | 66 | 3 | 3 | 3 | 25 | 26 | 28 |
| Min | 55 | 37 | 35 | 1 | 1 | 2 | 16 | 16 | 17 |
| StE | 2.48 | 3.48 | 3.39 | 0.25 | 0.29 | 0.18 | 1.00 | 1.16 | 1.34 |
| Sum | 506 | 449 | 437 | 18 | 17 | 19 | 175 | 162 | 174 |
| McGill Score | | | Day 1: 87.37; Day 5: 78.49; Day 10: 78.84 | | | | | | |

Less improvement was observed on the Affective aspects, and no effect was observed on the Evaluative part of the Questionnaire. Following this trend, treatment with 70 mg of RBE resulted in 41% reduction of pain as evaluated by Sensory part, but the total score of McGill Questionnaire for this experimental group yielded a 33% reduction after day 10. It is also interesting to notice that 5 days of treatment with 70 mg of RBE already resulted in 33% reduction of pain (total McGill score). This indicates that treatment with RBE may provide a moderately rapid effect (although not as acute as the effects of painkiller drugs such as NSAIDS). Exit interviews of study participants revealed that the first subjective improvements in pain were noticed after 3 days of the treatment. This observation strongly suggests that a 3 day time-point should be included in any future RBE clinical efficacy study protocol to follow rapid activity and effect on improvement of OA pain-related conditions.

Blood Chemistry Analysis.

Standard serum biochemistry analysis was performed on each serum collected at day 1 and day 10. No unusual changes were noticed in any parameters. All parameters were within normal range (data not shown).

Subjective Energy Tests.

In parallel to Mc-Gill Questionnaire, all participants were required to answer 4 questions pertaining to their physical strength rate (Q1), mental alertness (Q2), physical endurance rate (Q3) and mood rate (Q4). Rates for all these questions were scaled 1-4. This Questionnaire (described in this article as Energy Score) was performed at day 1, 5 and 10. The highest number indicated a generally elevated level of the feeling rate.

All detailed data of this Questionnaire are presented in Table 6. These data show that all participants reported feelings of increased mental alertness, strength, endurance, and mood in the dose dependent manner after treatment with RBE. Treatment with 70 mg resulted in 122% improvement over Day 1 (Table 6), whereas the treatment with RBE at dose 100 mg resulted in 81% improvement, indicating that treatment with the lower dose of 70 mg was optimal. Therefore, as it was noticed when analyzing McGill data, 70 mg dose seems to be the most potent for improvement of parameters listed in Table 6. Also, the lowest dose of 35 mg still provided significant Energy Scores increases of up to 74% after 10 days of the treatment. In comparison, the McGill data for the same dose resulted in only 11% improvement. This may indicate that a primary effect of RBE is to modulate feelings of energy, mood, endurance and awareness since dose as low as 35 mg caused improvement of Energy score up to 74%. These results were rather unexpected since the Energy Score was followed only as an additional subjective parameter to supplement the McGill pain score.

TABLE 6

| | Day 1 | | | | Day 5 | | | | Day 10 | | | |
|---|---|---|---|---|---|---|---|---|---|---|---|---|
| | Q1 | Q2 | Q3 | Q4 | Q1 | Q2 | Q3 | Q4 | Q1 | Q2 | Q3 | Q4 |
| Group 1 | | | | | | | | | | | | |
| Average | 1.14 | 1.28 | 1.28 | 1.42 | 1.42 | 2.14 | 1.71 | 2.48 | 2.14 | 2.28 | 2.57 | 2.57 |
| StD | 0.37 | 0.48 | 0.48 | 0.53 | 0.53 | 0.37 | 0.48 | 0.78 | 0.69 | 0.95 | 0.97 | 0.97 |
| Max | 2 | 2 | 2 | 2 | 2 | 3 | 2 | 4 | 3 | 4 | 4 | 4 |
| Min | 1 | 1 | 1 | 1 | 1 | 2 | 1 | 2 | 1 | 1 | 1 | 2 |
| StE | 0.14 | 0.45 | 0.45 | 0.20 | 0.20 | 0.14 | 0.18 | 0.29 | 0.26 | 0.35 | 0.36 | 0.36 |
| Sum | 9 | 9 | 9 | 10 | 10 | 15 | 12 | 17 | 15 | 16 | 18 | 18 |
| Energy Score | 9.25 +/− 0.5 | | | | 13.5 +/− 3.1 | | | | 16.75 +/− 1.5 | | | |
| Average Sum +/− StD | | | | | | | | | 81% increase over day 1 | | | |
| Group 2 | | | | | | | | | | | | |
| Average | 1.12 | 1.12 | 1.25 | 1.12 | 2.00 | 2.00 | 2.25 | 2.00 | 2.37 | 2.65 | 2.50 | 2.50 |
| StD | 0.35 | 0.35 | 0.46 | 0.35 | 1.30 | 1.06 | 0.88 | 0.00 | 1.40 | 1.18 | 0.92 | 0.92 |
| Max | 2 | 2 | 2 | 2 | 4 | 4 | 4 | 2 | 4 | 4 | 4 | 4 |
| Min | 1 | 1 | 1 | 1 | 1 | 1 | 1 | 2 | 1 | 1 | 2 | 2 |
| StE | 0.12 | 0.12 | 0.16 | 0.12 | 0.46 | 0.37 | 0.31 | 0.00 | 1.40 | 1.18 | 0.32 | 0.32 |
| Sum | 8 | 9 | 10 | 9 | 16 | 16 | 18 | 16 | 19 | 21 | 20 | 20 |
| Energy Score | 9.0 +/− 0.81 | | | | 16.5 +/− 1.0 | | | | 20.0 +/− 0.81 | | | |
| Average Sum +/− StD | | | | | | | | | 122% over Day 1 | | | |
| Group 3 | | | | | | | | | | | | |
| Average | 1.14 | 1.28 | 1.28 | 1.57 | 1.57 | 1.42 | 1.71 | 2.14 | 2.00 | 2.14 | 2.42 | 2.14 |
| StD | 0.37 | 0.48 | 0.48 | 0.53 | 0.53 | 0.53 | 0.48 | 0.69 | 0.5 | 0.37 | 0.97 | 0.69 |
| Max | 2 | 2 | 2 | 2 | 2 | 2 | 2 | 3 | 3 | 3 | 4 | 3 |
| Min | 1 | 1 | 1 | 1 | 1 | 1 | 1 | 1 | 1 | 2 | 1 | 1 |
| StE | 0.14 | 0.18 | 0.18 | 0.18 | 0.20 | 0.20 | 0.18 | 0.26 | 0.21 | 0.14 | 0.36 | 0.26 |
| Sum | 8 | 9 | 9 | 11 | 11 | 10 | 12 | 15 | 14 | 15 | 17 | 15 |
| Energy Score | 8.75 +/− 1.5 | | | | 12.0 +/− 2.16 | | | | 15.25 +/− 1.25 | | | |
| Average Sum +/− StD | | | | | | | | | 77% over Day 1 | | | |

Data collected on the Energy and McGill scores shows that RBE may indeed provide relief for conditions associated with OA. According to the working hypothesis mentioned at the beginning of this article, betalains may improve OA conditions due to their inhibitory effect on the chlorination of protein by hypochlorous acid released from activated neutrophils. This hypothesis was based on two rationales: 1.) that betalains can reduce the amount of hypochlorous acid generated by activated neutrophils; and 2.) that chlorinated proteins may contribute to onset of Osteoarthritis and associated conditions.

In order to begin testing this hypothesis, the serum levels of Advanced Oxidation Protein Products (AOPP) were measured using a commercial kit (Cell Biolabs, Inc., #STA318). This assay measures serum proteins modified by chloramine or hypochlorous acid. The detailed collected data are summarized in Table 7. The data show significant broad range (Max and Min) in baseline of AOPP at day 1 in each experimental group. Interestingly, this range was significantly reduced in each group after 10 days of the treatment. Resulting Sum data show 36.3, 47.6 and 30.9% reduction in groups 1, 2 and 3, respectively. However, due to the broad range of AOPP values at day 1, StD is relatively high. Consequently, these results are presented herein only as indicative and as a justification for further clinical investigation on OA subjects with increased serum AOPP levels.

TABLE 7

| | Group 1 | | Group 2 | | Group 3 | |
|---|---|---|---|---|---|---|
| Result | Day 1 | Day 10 | Day 1 | Day 10 | Day 1 | Day 10 |
| Average | 20.9 | 13.2 | 21.4 | 12.8 | 19.2 | 15.21 |
| Std | 14.9 | 7.2 | 12.4 | 7.3 | 8.0 | 4.9 |
| Max | 50.8 | 23.7 | 44.0 | 25.4 | 33.9 | 25.4 |
| Min | 7.8 | 6.8 | 8.7 | 5.0 | 8.5 | 10.2 |
| Sum | 144.6 | 92.2 | 171 | 89.7 | 154 | 106.5 |
| % Reduction in Average values | | | | | | |
| | 36.9 | | 50.2 | | 20.8 | |
| % Reduction in Sum values | | | | | | |
| | 36.3 | | 47.6 | | 30.9 | |

AOPP is known as a pro-inflammatory factor and inducer of TNF-alpha release from monocytes. Therefore it was reasonable to verify whether treatment with RBE may result in reduction of blood TNF-alpha levels. In order to further investigate possible actions of betalains, sera from volunteers treated with RBE were subjected to a Cytokines and Chemokines array as offered by Qynsys Inc. Collected data showed that prior to treatment only 10 participants out of 24 were found to have TNF-alpha above the detection limit of 1 pg/mL per Elisa assay. However, treatment with RBE caused reduction of TNF-alpha in these 10 subjects after 10 days of the treatment (Table 8). The same sera were additionally tested for changes in the levels of other cytokines and chemokines. This screening yielded data showing that treatment with RBE reduced serum level of IL6, GRO-alpha, and RANTES levels after 10 days of the treatment. (Table 8). H

TABLE 8

| 1 Subject | 2 Group | 3 TNF-alpha | 4 IL-6 | 5 GRO-alpha | 6 RANTES |
|---|---|---|---|---|---|
| 1 | 1 | 1.25 | 1.77 | 318 | 251442 |
|  |  | 1.00 | 1.62 | 235.0 | 218310 |
| 2 |  | 30.24 | 146 | 123.5 | 37542 |
|  |  | 28.43 | 135.9 | 64.6 | 27109 |
| 3 |  | 2.76 | 3.9 | 257.5 | 36127 |
|  |  | 1.16 | 2.2 | 227.0 | 33248 |
| DOD1 |  | 28.0% | 23.7% | 29.0% | 16.6% |
| N |  | 3 | 3 | 3 | 3 |
| 4 | 2 | 3.05 | ND | 113.5 | 23800 |
|  |  | 1.42 |  | 26.7 | 10099 |
| 5 |  | 1.43 | 6.65 | 70.9 | 30582 |
|  |  | 1.37 | 5.70 | 51.3 | 23821 |
| 6 |  | 2.24 | 2.59 | 504.3 | 380997 |
|  |  | 1.11 | 1.86 | 306.9 | 211381 |
| 7 |  | 116.07 | 476.2 | 120.2 | 27932 |
|  |  | 80.99 | 379.5 | 19.4 | 25647 |
| DOD1 |  | 35.0% | 22.0% | 57.2% | 33.7% |
| N |  | 4 | 3 | 4 | 4 |
| 8 | 3 | 1.34 | 4.7 | 73.3 | 15252 |
|  |  | 1.12 | 3.3 | 63.9 | 13115 |
| 9 |  | 1.70 | 2.2 | 48.5 | 36672 |
|  |  | 1.61 | 1.2 | 32.4 | 17600 |
| 10 |  | 172.35 | 293.2 | 135.2 | 15826 |
|  |  | 171.88 | 268.5 | 116.5 | 10265 |
| DOD1 |  | 8.3% | 28.3% | 21.0% | 34.0% |
| N |  | 3 | 3 | 3 | 3 |

These data indicate that RBE may have favorable effect on blood levels of TNF-alpha, IL-6, RANTES, and GRO-alpha. Due to rather limited number of participants per group showing serum level of TNF-alpha higher than 1 pg/mL, data in Table 8 are presented as indicative rather than definite. Here, the effect of RBE is shown on blood level of selected cytokines and chemokines in subjects with TNF-alpha blood level >1 pg/mL. All other cytokines and chemokines are presented at concentration pg/mL. Upper number in raw represents level of measured peptide at day 1, bottom number at day 10. DOD1=change in peptide level at day 10 over day 1 and expressed as % of change It should be noted that subjects with initial serum levels of TNF-alpha below 1 pg/mL also reported reduction of McGill scores and improvements on Energy. This observation suggests that RBE may improve McGill and Energy score in OA subjects in a TNF-alpha-independent manner. Measurement of blood levels of selected cytokines and chemokines indicated that TNF-alpha, IL-6, GRO-alpha, and RANTES could be reduced after 10 days of the treatment. It was also observed that initial blood levels of AOPP were reduced during 10 days of the treatment, confirming that betalains present in RBE may reduce detrimental effect of hypochloric acid in human subjects.

Sinusitis, contact dermatitis, and acne tests were performed by administration of the betalain compositions as reported for OA above using daily dosage of 70 mg of the betalain composition. All subjects reported subjective results on a bar scale and measurements were taken to digitize the response as known in the art.

For treatment of sinusitis, Table 9 below illustrates exemplary results for various listed parameters:

TABLE 9

| Subject # and Initials | Question | Score at day 1 | Score at Day 7 | Overall % Improvement at day 7 |
|---|---|---|---|---|
| #1: PTC | Intensity of nasal drainage | 44 | 38 | 14 |
| Age: 31 | Intensity of headache | 76 | 4 | 95 |
| Gender: M | Intensity of facial pain-pressure | 4 | 2 | 50 |
| Weight: 175 | Intensity of watery/red eyes | 121 | 37 | 70 |
| Height: 5'11 | Intensity of itchy/palate nose | 94 | 71 | 25 |
| Case: Sinusitis | Intensity of nasal congestion | 95 | 44 | 54 |
|  | Fatigue level | 31 | 8 | 75 |
|  | Intensity of skin itching | 71 | 31 | 57 |
|  | Intensity of skin dryness | 74 | 3 | 96 |
|  | Average improvement |  |  | 59.6% |
| #1: LS | Intensity of nasal drainage | 68 | 1 | 99 |
| Age: 24 | Intensity of headache | 33 | 1 | 97 |
| Gender: F | Intensity of facial pain-pressure | 15 | 8 | 47 |
| Weight: 208 | Intensity of watery/red eyes | 1 | 1 | 0 |
| Height: 5'7" | Intensity of itchy/palate nose | 135 | 124 | 9 |
| Case: Sinusitis | Intensity of nasal congestion | 114 | 31 | 73 |
|  | Fatigue level | 131 | 66 | 50 |
|  | Intensity of skin itching | 104 | 106 | 1 |
|  | Intensity of skin dryness | 135 | 135 | 0 |
|  | Average Improvement |  |  | 41.7 |

For treatment of eczema and contact dermatitis, Table 10 below illustrates exemplary results for various listed parameters:

TABLE 10

Treatment of subjects suffering Chronic skin allergy

Visual Analog Score Evaluation

| Subject # and Initials | Question | Score at day 1 | Score at Day 7 | Score at Day 14 | Overall % Improvement at day 7 and 14 |
|---|---|---|---|---|---|
| #1: GVR | Intensity of skin redness in affected area | 81 | 17 | 11 | 80 & 87 |
| Age: 38 | Intensity of itching in the morning | 4 | 4 | 4 | 0 |
| Gender: M | Intensity of itching at bedtime | 5 | 5 | 5 | 0 |
| Weight: 215 | Average size of red spots | 26 | 11 | 8 | 58 & 70 |
| Height: 6'2 | Intensity of skin pain in affected areas | 6 | 5 | 6 | 0 |
| Case: | Intensity of skin dryness in affected areas | 19 | 11 | 17 | 43 & 11 |
| Dermatitis | Intensity of your nervousness | 8 | 6 | 7 | 0 |
| | Frequency of allergic skin reactions | 13 | 6 | 6 | 54 & 54 |
| | Intensity of skin tension in affected area | 13 | 6 | 5 | 54 & 62 |
| | Average Improvement after day 7 and 14 | | | | 26.5 & 31.5 |
| #1: NS | Intensity of skin redness in affected area | 28 | 10 | NT | 65 |
| Age: 46 | Intensity of itching in the morning | 128 | 2 | NT | 98 |
| Gender: F | Intensity of itching at bedtime | 128 | 2 | NT | 98 |
| Weight: 183 | Average size of red spots | 40 | 2 | NT | 95 |
| Height: 5'8" | Intensity of skin pain in affected areas | 4 | 2 | NT | 50 |
| Case: | Intensity of skin dryness in affected areas | 12 | 4 | NT | 67 |
| Eczema | Intensity of your nervousness | 96 | 65 | NT | 33 |
| | Frequency of allergic skin reactions | 98 | 2 | NT | 98 |
| | Intensity of skin tension in affected area | 14 | 2 | NT | 86 |
| | Average Improvement | | | | 76.7 |

For treatment of acne, Table 11 below illustrates exemplary results for various listed parameters:

TABLE 11

| Subject # and Initials | Question | Score at day 1 | Score at Day 7 | Overall % Improvement at Day 7 and 14 |
|---|---|---|---|---|
| #1: BS | Size of acne lesions | Pinhead-2 mm | Pinhead, 1 mm | 50 |
| Age: 11 | # of lesions on face | 25 | 5 | 75 |
| Gender: M | # of lesions on neck | 0 | 0 | 0 |
| Weight: 103 | # of lesions on chest | 27 | 12 | 56 |
| Height: 5'4" | # of lesions on the back | 5 | 1 | 80 |
| | Average improvement | | | 52.2 |
| #2: SH | Size of Acne lesions | 3-5 mm | 2-3 mm | 38 |
| Age: 27 | # of lesions on face | 4 | 2 | 50 |
| Gender: F | # of lesions on neck | 4 | 2 | 50 |
| Weight: 145 | # of lesions on chest | 0 | 0 | 0 |
| Height: 5'1" | # of lesions on back | 2 | 1 | 50 |
| | Average Improvement | | | 37.6 |

Thus, specific embodiments and applications of treatment of various conditions using betalain-containing compositions have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of reducing joint pain in an individual, comprising:
    administering or providing for administration a dehydrated complex betalain mixture comprising a plurality of distinct betalains from a starting material, wherein the distinct betalains have a near natural composition and are present in the mixture at a total betalain concentration of at least 4 wt %;
    wherein the dehydrated complex betalain mixture further comprises a plurality of sugars, wherein a ratio of the plurality of distinct betalains to the one or more sugars is at least 0.3; and
    wherein the complex betalain mixture is formulated for oral administration and orally administered in an amount that reduces joint pain in the individual.

2. The method of claim 1, wherein the starting material is selected from a group consisting of a beet juice, a raw beet or a portion of the raw beet, a beet processing waste liquid, a beet root culture or culture supernatants, a plant material comprising one or more betalains, and a near natural betalain product.

3. The method of claim 1, wherein the starting material comprises beet juice.

4. The method of claim 1, wherein the total betalain concentration in the dehydrated complex betalain mixture is at least 10 wt %.

5. The method of claim 1, wherein the total betalain concentration in the dehydrated complex betalain mixture is at least 20 wt %.

6. The method of claim 1, wherein the dehydrated complex betalain mixture further comprises a plurality of sugars, wherein a ratio of the plurality of distinct betalains to the one or more sugars is at least 2.0.

7. The method of claim 1, wherein the dehydrated complex betalain mixture further comprises a plurality of sugars, wherein a ratio of the plurality of distinct betalains to the one or more sugars is between 2.5 and 4.5.

8. The method of claim 1, wherein the complex betalain mixture is formulated in a tablet or capsule that contained between 10 and 100 mg of the complex betalain mixture.

9. The method of claim 1, wherein the complex betalain mixture is formulated in a tablet or capsule that provides between 10 and 50 mg of total betalains.

10. The method of claim 1, wherein the complex betalain mixture further comprises a non-steroidal anti-inflammatory drug and/or a cylooxygenase (COX) inhibitor.

11. The method of claim 1, wherein the joint pain is due to osteoarthritis.

12. The method of claim 11, wherein the joint pain is knee pain.

13. The method of claim 1, wherein administering the dehydrated complex betalain mixture further reduces inflammation.

14. The method of claim 1, wherein administering the dehydrated complex betalain mixture further reduces swelling.

15. A method of reducing inflammation in an individual, comprising:

administering or providing for administration a dehydrated complex betalain mixture comprising a plurality of distinct betalains from a starting material, wherein the distinct betalains have a near natural composition and are present in the mixture at a total betalain concentration of at least 4 wt %;

wherein the dehydrated complex betalain mixture further comprises a plurality of sugars, wherein a ratio of the plurality of distinct betalains to the one or more sugars is at least 0.3; and wherein the complex betalain mixture is formulated for oral administration and orally administered in an amount that reduces inflammation in the individual.

16. The method of claim 15, wherein the total betalain concentration in the dehydrated complex betalain mixture is at least 10 wt %.

17. The method of claim 15, wherein the dehydrated complex betalain mixture further comprises a plurality of sugars, wherein a ratio of the plurality of distinct betalains to the one or more sugars is at least 2.0.

18. The method of claim 15, wherein the complex betalain mixture is formulated in a tablet or capsule that contained between 10 and 100 mg of the complex betalain mixture.

19. The method of claim 15, wherein the complex betalain mixture is formulated in a tablet or capsule that provides between 10 and 50 mg of total betalains.

20. The method of claim 15, wherein the complex betalain mixture further comprises a non-steroidal anti-inflammatory drug and/or a cylooxygenase (COX) inhibitor.

* * * * *